United States Patent [19]

Holt et al.

[11] 4,110,305

[45] Aug. 29, 1978

[54] POLYMERS STABILIZED BY ESTERS OF PIPERIDINOLS

[75] Inventors: Brian Holt, Oldham; Donald Richard Randell, Stockport, both of England

[73] Assignee: Ciba-Geigy Corporation, Ardsley, N.Y.

[21] Appl. No.: 741,813

[22] Filed: Nov. 15, 1976

Related U.S. Application Data

[60] Division of Ser. No. 475,718, Jun. 3, 1974, Pat. No. 3,992,390, which is a continuation-in-part of Ser. No. 309,853, Nov. 27, 1972, abandoned.

[30] Foreign Application Priority Data

Nov. 30, 1971 [GB] United Kingdom ............... 55486/71

[51] Int. Cl.$^2$ ................................................. C08K 5/34
[52] U.S. Cl. ............................................. 260/45.8 N
[58] Field of Search ................................... 260/45.8 N

[56] References Cited

U.S. PATENT DOCUMENTS

| | | | |
|---|---|---|---|
| 3,435,065 | 3/1969 | Dexter et al. .................. | 260/45.8 N |
| 3,640,928 | 2/1972 | Murayama et al. ............ | 260/45.8 N |
| 3,833,636 | 9/1974 | Holt et al. ...................... | 260/45.8 N |
| 3,840,494 | 10/1974 | Murayama et al. ............ | 260/45.8 N |
| 3,984,371 | 10/1976 | Murayama et al. ............ | 260/45.8 N |
| 3,993,655 | 11/1976 | Rasberger et al. ............. | 260/45.8 N |

*Primary Examiner*—V. P. Hoke
*Attorney, Agent, or Firm*—Vincent J. Cavaliere

[57] ABSTRACT

New alkyl substituted p-hydroxy aryl esters and alkyl substituted p-hydroxy aralkyl esters of 2,2,6,6-tetrasubstituted piperidin-4-ols are used as stabilizers for organic materials, especially for polymers.

7 Claims, No Drawings

POLYMERS STABILIZED BY ESTERS OF PIPERIDINOLS

This is a divisional of application Ser. No. 475,718 filed on June 3, 1974 now U.S. Pat. No. 3,992,390, which in turn was a continuation-in-part of Ser. No. 309,853, filed Nov. 27, 1972, now abandoned.

The present invention concerns new piperidine derivatives and in particular new alkyl substituted p-hydroxy aryl esters or alkyl substituted p-hydroxy aralkyl esters of 2,2,6,6-tetrasubstituted piperidin-4-ols useful as stabilisers for polymers, especially polypropylene.

In German Patent Specification No. 1,929,928 there are described compounds of the general formula:

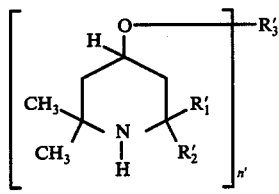

wherein $R_1'$ and $R_2'$ are the same or different and are, for example, methyl groups, n' = 1 to 3 and $R_3'$, where n' = 1, is inter alia, an acyl group derived from certain classes of mono-carboxylic acids. In the case of aromatic monocarboxylic acids, only unsubstituted methyl chlorine-substituted aryl and aralkyl carboxylic acids are specified.

We now describe a new class of esters derived from aryl and aralkyl carboxylic acids substituted in the aryl moiety by both hydroxyl and alkyl groups.

According to the present invention, there are provided compounds having the general formula:

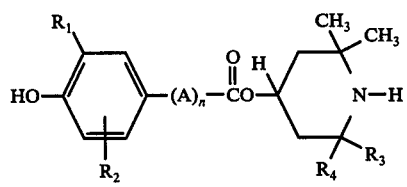

wherein A is —CH$_2$—, —CH$_2$CH$_2$— or $$-CH_2-CH-,\\ \qquad\quad |\\ \qquad\quad CH_3$$

$R_1$ and $R_2$ are the same or different and each is a straight- or branched-chain alkyl group having from 1 to 6 carbon atoms, or 1-methylcyclohexy or α,α-dimethylbenzyl, $R_3$ and $R_4$ are the same or different and each is an alkyl group having from 1 to 12, preferably 1 to 6, carbon atoms or $R_3$ and $R_4$ together with the carbon atom to which they are bound form a saturated alicyclic residue having from 5 to 8 carbon atoms or the group of formula-:

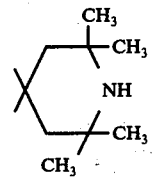

and n is 0 or 1.

Examples of $R_1$ and $R_2$, are methyl, ethyl, n-propyl, isopropyl, sec-butyl, t-butyl, t-pentyl (1,1-dimethylpropyl and t-hexyl (1,1-dimethylbutyl). Preferably one or both of $R_1$ and $R_2$ are t-butyl, although it will be understood that t-butyl is a bulky group and that consequently it is unlikely that two such groups will be situated on adjacent carbon atoms of the phenyl nucleus.

Examples of $R_3$ and $R_4$ are methyl, ethyl, iso-propyl, n-butyl, n-hexyl, n-octyl, or n-dodecyl. Preferably, however, $R_3$ and $R_4$ are each a methyl group.

Compounds of formula I are preferred in which the grouping A is —CH$_2$,CH$_2$— and n is 1; other preferred groups of compounds are those in which n is 0.

Preferred compounds of formula I are those having the formulae II and III:

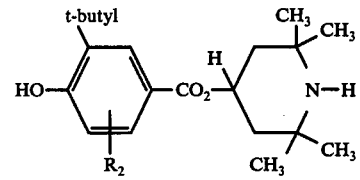

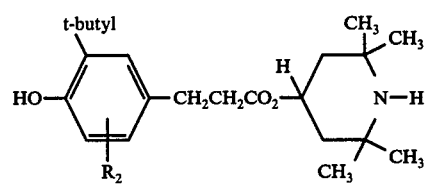

In the formulae II and III, $R_2$ is preferably a t-butyl group attached ortho to the hydroxyl group or a methyl group attached ortho or meta to the hydroxyl group.

The present invention also provides a first process in which the compounds of formula I are produced, comprising reacting the piperidino of formula IV:

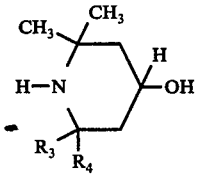

with an acid halide having the formula:

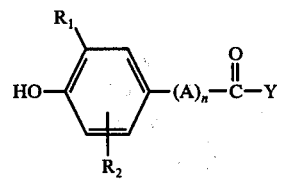

wherein $R_1$, $R_2$, A and n have their previous significance and Y is halogen, preferably chlorine, in the presence of a halogen acid binding substance, for example, a base such as triethylamine; on the other hand, an excess of the amine reactant serves adequately as a halogen acid binding compound.

According to the present invention, there is also provided a second process in which a compound of formula I is produced comprising reacting a compound of formula IV with an ester having the formula:

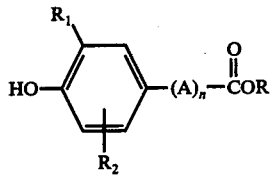

VI wherein R is an alkyl group having from 1 to 6 carbon atoms, preferably a methyl or ethyl group, in the presence of a transesterification catalyst such as an alkali metal amide, for instance lithium amide.

The second process according to the invention is conveniently effected by fusing the reactants together and agitating the molten mass until the reaction is complete, as determined, for example by collecting the alcohol produced in the reaction and stopping the reaction when the theoretical amount of alcohol has been removed.

The present invention provides also a third, less preferred process in which a compound of formula I is produced, comprising reacting the piperidinol of formula IV with a carboxylic acid having the formula:

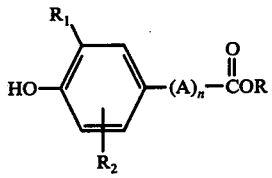

VII wherein $R_1$, $R_2$, A and n have their previous significance, in the presence of an esterification catalyst, which is preferably a neutral catalyst, for instance a tetraalkyl titanate.

The starting materials of formulae V, VI and VII may all be prepared by methods well known per se.

Specific compounds of formula I include the following:

2,2,6,6-Tetramethylpiperidinyl-4-3',5'-dimethyl-4'-hydroxybenzoate
2,2,6,6-Tetramethylpiperidinyl-4-β(3',5'-dimethyl-4'-hydroxyphenyl) propionate
2,2,6,6-Tetramethylpiperidinyl-4-3',5'-diisopropyl-4'-hydroxybenzoate
2,2,6,6-Tetramethylpiperidinyl-4-β(3',5'-di-isopropyl-4'-hydroxyphenyl)propionate
2,2,6,6-Tetramethylpiperidinyl-4-3'-t-butyl-5'-methyl-4'-hydroxybenzoate
2,2,6,6-Tetramethylpiperidinyl-4-β(3'-t-butyl-5'-methyl-4'-hydroxyphenyl)propionate
2,2,6,6-Tetramethylpiperidinyl-4-(β(-3'-t-butyl-6'-methyl-4'-hydroxyphenyl)propionate
2,2,6,6-Tetramethylpiperidinyl-4-3'-di-t-butyl-4'-hydroxybenzoate
2,2,6,6-Tetramethylpiperidinyl-4-(3',5'-di-t-butyl-4'-hydroxyphenyl)acetate
2,2,6,6-Tetramethylpiperidinyl-4-β(3',5'-di-t-butyl-4'-hydroxyphenyl)propionate
1-Aza-4-[3',5'-di-t-butyl-4'-hydroxybenzoyloxy]-2,2-dimethylspiro[5,5]undecane
1-Aza-4-[-β(3',5'-di-t-butyl-4'-hydroxyphenyl)propionoxy]-2,2-dimethylspiro[5,5]undecane
1,9-Diaza-4-[3',5'-di-t-butyl-4'-hydroxybenzoyloxy]-2,2,8,8,10,10-octamethylspiro[5,5]undecane
2,2,6,6-Tetramethylpiperidinyl-4-[3',5'-bis(α,α-dimethylbenzyl)-4'-hydroxybenzoate]
2,2,6,6-Tetramethylpiperidinyl-4-[3',5'-bis(1"-methylcyclohexyl)-4'-hydroxyphenyl]propionate The present invention still further provides a composition comprising an organic material and a stabilising amount of a compound having the Formula I as hereinbefore defined.

Compounds of formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methylbutene-1, hexene-1, 4-methylpentene-1, 4-methylhexene-1 and 4,4-dimethyl-pentene-1, and also co- and terpolymers of olefines, particularly of ethylene or propylene.

Other organic material susceptible to degradation by the effects of light and the properties of which are improved by the incorporation therein of a compound of Formula I include natural and synthetic polymeric materials, for instance natural and synthetic rubbers, the latter including, for example, homo-, co- and terpolymers of acrylonitrile, butadiene and styrene.

Specific synthetic polymers include polyvinyl chloride, polyvinylidene chloride and vinyl chloride copolymers, polyvinyl acetate as well as condensation polymers derived from ether, ester (derived from carboxylic sulphonic or carbonic acids), amide or urethane groupings. These polymers can, for instance, form the basis of surface coating media such as paints and lacquers having an oil or resin, for instance an alkyd or polyamide resin base.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound of formula I may be added to the polymer during the preparation of the latter, for instance at the latex stage of polymer production, to provide pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binary, tertiary and multi-component compositions containing the stabiliser of formula I together with one or more functional additives for polymers.

Examples of suitable antioxidants are those of the hindered phenol type such as those selected from the following groups:

(1) Phenolic compounds having the general formula

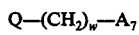
Q—(CH$_2$)$_w$—A$_7$ wherein Q is

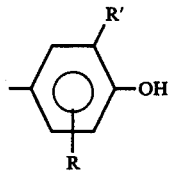

A$_1$ is —CR(COOR")$_2$

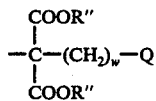

R is hydrogen or lower alkyl
R' is lower alkyl
R" is alkyl group having from 6 - 24 carbon atoms
$w$ is an integer from 0 to 4.

Illustrative examples of the compounds shown above are di-n-octadecyl α-(3,5-di-t-butyl-4-hydroxybenzyl)-malonate di-n-octadecyl α-(3-t-butyl-4-hydroxy-5-methyl-benzyl)-malonate which is disclosed in the Netherlands Patent No. 6,711,199, Feb. 19, 1968 di-n-octadecyl-α,α'bis-(3-t-butyl-4-hydroxy-5-methylbenzyl) malonate which is disclosed in the Netherlands Patent No. 6,803,498, Sept. 18, 1968.

(2) Phenolic compounds having the general formula

Q—R

Illustrative examples of the compounds shown above are
2,6-di-t-butyl-p-cresol
2-methyl-4,6-di-t-butylphenol and the like.
2,6-di-Octadecyl-p-cresol (3) Phenolic compounds having the formula

Q—C$_w$H$_{2w}$—Q are:-
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-metylene-bis[6-(2-t-methylcyclohexyl)-4-methylphenol
2,2'-methylene-bis(3-t-butyl-5-ethylphenol)
4,4'-methyl-bis(3,5-di-t-butylphenol)
4,4'-methylene-bis(3-t-butyl-5-methylphenol)
2,2'-methylene-bis(3-t-butyl-5-methyl-phenol) and the like (4) Phenolic compounds having the formula

R—O—Q

Illustrative examples of such compounds are 2,5-di-t-butylhydroquinone
2,6-di-t-butylhydroquinone
2,5-di-t-butyl-4-hydroxyanisole (5) Phenolic compounds having the formula

Q—S—Q

Illustrative examples of such compounds are
4,4'-thiobis-(2-t-butyl-5-methylphenol)
4,4'-thiobis-(2-t-butyl-6-methylphenol)
2,2'-thiobis-(6-t-butyl-4-methylphenol)
4,4'-thiobis-(2-methyl-5-t-butylphenol)

(6) Phenolic compounds having the formula

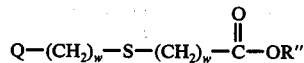
Q—(CH$_2$)$_w$—S—(CH$_2$)$_w$—C(=O)—OR"

Illustrative examples of such compounds are
octadecyl-(3,5-dimetyl-4-hydroxybenzylthio)-acetate
dodecyl-(3,5-di-t-butyl-4-hydroxybenzylthio)-propionate (7) Phenolic compounds having the formula

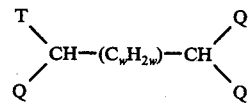

wherein T is hydrogen
R or Q as defined above.

Illustrative examples of such compounds are
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane (8) Phenolic compounds having the formula

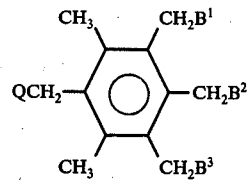

wherein B$^1$, B$^2$ and B$^3$ are hydrogen, methyl or provided that when B$^1$ and B$^3$ are Q then B$^2$ is hydrogen or methyl and when B$^2$ is Q then B$^1$ and B$^3$ are hydrogen or methyl.
Illustrative examples of such compounds are
1,4-di(3,5-di-t-butyl-4-hydroxybenzyl)-2,3,5,6-tetramethylbenzene 1,3,5-tri(3,5-di-t-butyl-4-hydroxybenzyl)-2,4,6-trimethylbenzene (9) Phenolic compounds having the formula

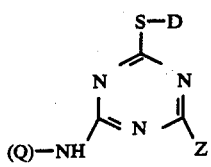

wherein

Z is NHQ, —S—D or —O—Q

D is alkyl group having from 6–12 carbon atoms or —($C_wH_{2w}$)—S—R''

Illustrative examples of such compounds are 2,4-bis-(n-octylthio)-6-(3,5-di-t-butyl-4-hydroxyaniline)-1,3,5-triazine 6-(4-hydroxy-3-methyl-5-t-butylanilino)-2,4-bis-(n-octylthio)-1,3,5-triazine 6-(4-hydroxy-3,5-dimethylanilino)-2,4-bis-(n-octylthio)-1,3,5-triazine 6-(4-hydroxy-3,5-di-t-butylanilino)-2,4-bis-(n-octylthio)-1,3,5-triazine.

6-(4-hydroxy-3,5-di-t-butylanilino)-4-(4-hydroxy-3,5-di-t-butylphenoxy)-2-(n-octylthio)-1,3,5-triazine 2,4-bis(4-hydroxy-3,5-di-t-butylanilino)-6-(n-octylthio)-1,3,5-triazine.

The above phenolic triazine stabilizers are more fully described in U.S. Pat. No. 3,255,191.

(10) Phenolic compounds having the formula

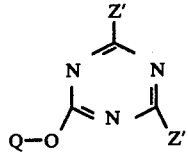

wherein Z' is —O—Q, —S—D or —S—($C_wH_{2w}$)—SD

Illustrative examples of such compounds are 2,3-bis-(3,5-di-t-butyl-4-hydroxyphenoxy)-6-(n-octylthio)-1,3,5-triazine 2,4,6-tris-(4-hydroxy-3,5-di-t-butylphenoxy)-1,3,5-triazine.

6-(4-hydroxy-3,5-di-t-butylphenoxy)-2,4-bis-(n-octylthiocthylthio)-1,3,5-triazine 6-(4-hydroxy-3-methylphenoxy)-2,4-bis-(n-octylthio)-1,3,5-triazine 6-(4-hydroxy-;b 3-t-butylphenoxy)-2,4-bis-(n-octylthioethylthio)-1,3,5-triazine 6-(4-hydroxy-3-methyl-5-t-butylphenoxy)-2,4-bis-(n-octylthio)-1,3,5-triazine 2,4-bis-(4-hydroxy-3-methyl-5-t-butylphenoxy)-6-(n-octylthio)-1,3,5-triazine 2,4,6-tris-(4-hydroxy-3-methyl-5-t-butylphenoxy)-1,3,5-triazine 6-(4-hydroxy-3,5-di-t-butylphenoxy)-2,4-bis-(n-octylthiopropylthio)-1,3,5-triazine 6-(4-hydroxy-3,5-di-t-butylphenoxy)-2,4-bis-(n-dodecylthioethylthio)-1,3,5-triazine 2,4-bis-(4-hydroxy-3,5-di-t-butylphenoxy)-6-butylthio-1,3,5-triazine 2,4-bis-(4-hydroxy-3,5-di-t-butylphenoxy)-6-(n-octadecylthio)-1,3,5-triazine 2,4-bis-(4-hydroxy-3,5-di-t-butylphenoxy)-6-(n-dodecylthio)-1,3,5-triazine 2,4-bis-(4-hydroxy-3,5-di-t-butylphenoxy)-6-(n-octylthiopropylthio)-1,3,5-triazine 2,4-bis-(4-hydroxy-3,5-di-t-butylphenoxy)-6-(n-octylthioethylthio)-1,3,5-triazine 2,4-bis-(4-hydroxy-3,5-di-t-butylphenoxy-6-(n-dodecylthioethylthio)-1,3,5-triazine.

The above phenolic triazine stabilizers are more fully described in U.S. Pat. No. 3,255,191.

(11) Phenolic compounds having the formula

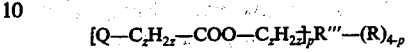

wherein p is an integer from 2 to 4 and R''' is a tetravalent radical selected from aliphatic hydrocarbons having from 1 to 30 carbon atoms aliphatic mono and dith oethers having from 1 to 30 carbon atoms aliphatic mono and diethers having from 1 to 30 carbon atoms and z is an integer from 0 to 6.

Illustrative examples of such compounds are

SUB-CLASS I n-Octadecyl 3-(3,5-di-t-butyl-4-hydroxyphenyl)-propionate n-Octadecyl 2-(3,5-di-t-butyl-4-hydroxyphenyl)-acetate n-Octadecyl 3,5-di-t-butyl-4-hydroxybenzoate n-Hexyl 3,5-di-t-butyl-4-hdroxyphenylbenzoate n-Dodecyl 3,5-di-t-butyl-4-hydroxyphenylbenzoate Neo-dodecyl 3-(3,5-di-t-butyl-4-hydroxyphenyl)-propionate Dodecyl β-(3,5-di-t-butyl-4-hydroxyphenyl)-propionate Ethyl α-(4-hydroxy-3,5-di-t-butylphenyl)-isobutyrate Octadecyl α-(4-hydroxy-3,5-di-t-butylphenyl)-isobutyrate Octadecyl α-(4-hydroxy-3,5-di-t-butylpenyl)-propionate

SUB-CLASS II 2-(n-octylthio)ethyl 3,5-di-t-butyl-4-hydroxybenzoate 2-(n-octylthio)ethyl 3,5-di-t-butyl-4-hydroxyphenylacetate 2-(n-octadecylthio)ethyl 3,5-di-t-butyl-4-hydroxyphenylacetate 2-(n-octadecylthio)ethyl 3,5-di-t-butyl-4-hydroxy benzoate 2-(2-hydroxyethylthio)ethyl 3,5-di-t-butyl-4-hydroxybenzoate 2,2'-Thiodiethanol bis(3,5-di-t-butyl-4-hydroxyphenyl)acetate Diethyl glycol bis-[3,5-di-t-butyl-4-hydroxyphenyl)propionate]

2-(n-octadecylthio)ethyl 3-(3,5-di-t-butyl-4-hydroxyphenyl)propionate 2,2'-Thiodiethanol-bis-3-(3,5-di-t-butyl-4-hydroxyphenyl)propionate Stearamido N,N-bis-[ethylene 3-(3,5-di-t-butyl-4-hydroxyphenyl)propionate]

n-Butylimino N,N-bis-[ethylene 3-(3,5-di-t-butyl-4-hydroxyphenyl)propionate ]

2-(2-stearoyloxyethylthio)ethyl 3,5-di-t-butyl-4-hydroxybenzoate 2-(2-hydroxyethylthio)ethyl 7(3-methyl-5-t-butyl-4-hydroxyphenyl)heptanoate 2-(2-stearoyloxyethylthio)ethyl 7-(3-methyl-5-t-butyl-4-hydroxyphenyl)heptanoate

SUB-CLASS III 1,2-propylene glycol bis-[3-(3,5-di-t-butyl-4-hydroxyphenyl)propionate]

Ethylene glycol bis-[3-(3,5-di-t-butyl-4-hydroxyphenyl)propionate]

Neopentylglycol bis-[3-(3,5-di-t-butyl-4-hydroxyphenyl)propionate]

Ethylene glycol bis-(3,5-di-t-butyl-4-hydroxyphenylacetate)

Glycerine-1-n-octadecanoate-2,3-bis-(3,5-di-t-butyl-4-hydroxyphenylacetate

Pentaethylthritol-tetrakis-[3-(3,5-di-t-butyl-4-hydroxyphenyl)propionate]

1,1,1-trimethylol ethane-tris-3-(3,5-di-t-butyl-4-hydroxyphenyl)propionate

Sorbitol hexa-[3-(3,5-di-t-butyl-4-hydroxyphenyl)propionate]

1,2,3-butanetriol tris-[3-(3,5-di-t-butyl-4-hydroxyphenyl)propionate]

2-hydroxyethyl 7-(3-methyl-5-t-butyl-4-hydroxyphenyl)heptanoate 2-stearoyloxyethyl 7-(3-methyl-5-t-butyl-4-hydroxyphenyl)heptanoate 1,6-n-hexanediol-bis[(3',5'-di-t-butyl-4-hydroxyphenyl) propionate]

The above phenolic ester stabilizers of sub-classes I, II and III are more fully described in U.S. Pat. No. 3,330,859.

(12) Phenolic compounds having the formula $$Q-(CH_2)_x-\overset{O}{\overset{\|}{P}}(OR'')_2$$

where x is an integer of 1 or 2.

Illustrative examples of such compounds are

Di-n-octadecyl 3,5-di-t-butyl-4-hydroxybenzylphosphonate

Di-n-octadecyl 3-t-butyl-4-hydroxy-5-methylbenzylphosphonate

Di-n-octadecyl 1-(3,5-di-t-butyl-4-hydroxyphenyl)ethanephosphonate

Di-n-tetradecyl 3,5-di-t-butyl-4-hydroxybenzylphosphonate

Di-n-hexadecyl 3,5-di-t-butyl-4-hydroxybenzylphosphonate

Di-n-docosyl-3,5-di-t-butyl-4-hydroxybenzylphosphonate

Di-n-octadecyl 3,5-di-t-butyl-4-hydroxybenzylphosphonate

The above di-(higher)alkyl phenolic phosphonates are more fully described in U.S. Pat. No. 3,281,505.

(13) Phenolic compounds having the formula $$\begin{array}{c} (CH_2)wQ \\ | \\ O=C-N-C=O \\ | \quad\quad\quad | \\ QW(H_2C)-N \quad\quad N-(CH_2)WQ \\ \diagdown \quad / \\ C \\ \| \\ O \end{array}$$

wherein w and Q are defined above.

Illustrative examples of such compounds are:

tris-(3,5-di-t-butyl-4-hydroxybenzyl)isocyanurate tris-(3-t-butyl-4-hydroxy-5-methylbenzyl)isocyanurate The above hydroxyphenylalkenyl isocyanurates are more fully described in U.S. Pat. No. 3,531,483.

The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:- phenyl-1-naphthylamine
phenyl-2-naphthylamine
N,N'-diphenyl-p-phenylenediamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include (a) 2-(2'-hydroxyphenyl)benzotriazoles, for instance 5'-methyl; 3',5'-di-t-butyl; 5'-t-butyl; 5-chloro-3',5'-di-t-butyl; 5-chloro-3'-t-butyl-5'-methyl; 3'-sec.butyl-5'-tert-butyl; 3'-[α-methylbenzyl]-5'-methyl-; 3'-[α-methylbenzyl]-5'-methyl-5-chloro-; 4'-octoxy-; 3',5'-di-t-amyl; 3'-methyl-5'-carbomethoxyethyl; 5-chloro-3',5'-di-t-amyl derivatives.

(b) 2,4bis-(2'-hydroxyphenyl)-6-alkyl-S-triazines, for instance the 6-ethyl or 6-undecyl derivatives.

(c) 2-hydroxybenzophenones, for instance the 4-hydroxy, 4-methoxy, 4-octoxy-, 4-decyloxy-, 4-dodecyloxy-, 4,2',4'-trihydroxy or 2'-hydroxy-4,4'-dimethoxy derivatives.

(d) 1,3-Bis(2'-hydroxybenzoyl)-benzenes for instance, 1,3bis-(2'-hydroxy-4'-hexyloxybenzoyl)benzene 1,3-bis-(2'-hydroxy-4'-octoxybenzoyl)benzene 1,3-bis-(2'-hydroxy-4'-dodecyloxybenzoyl)benzene (e) Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl-4-hydroxybenzoic acid-2,4-di-tert.butyl phenyl ester and - octadecyl ester and -2-methyl-4,6-di-tert.butyl phenyl ester.

(f) Acrylates, for instance α-Cyano-β,β-diphenylacrylic acid ethyl- or iso-octyl ester, α-carbomethoxycinnamic acid methyl- or butyl ester and N-(β-carbomethoxyvinyl)-2-methyl indoline.

(g) Nickel compounds such as nickel complexes of 2,2'-thiobis-(4-tert. octylphenol), for instance the 1:1 and 1:2 complexes, optionally having other ligands such as n-butylamine, triethanolamine or N-cyclohexyl-diethanolamine; nickel complexes of bis-(4-tert. octylphenyl) sulphone such as the 2:1 complex, optionally having other ligands such as 2-ethylcaproic acid; nickel dibutyl dithiocarbamates; nickel salts of 4-hydroxy-3,5-di-tert.butylbenzylphosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and (h) Oxalic acid diamides, for instance 4,4'-dioctyloxyoxanilide 2,2'-dioctyloxy-5,5'-di-tert.butyl-oxanimide 2,2'-di-dodecyloxy-5,5'-di-tert.butyl oxanilide 2-ethoxy-5-tertiarybutyl-2'-ethyl-oxanilide 2-ethoxy-2'-ethyl-oxanilide mixtures of o- and p- methoxy and ethoxy-disubstituted oxanilides and the compound of formula:

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert. butylphenyl) phosphite.

Peroxide-decomposing compounds for polyolefins include esters of β-thiodipropionic acids, for instance the lauryl- ,stearyl- , myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated polymeric material.

In binary combinations with one or more antioxidants listed above or in tertiary combinations with such antioxidants and U.V. absorbers listed above, the compounds of formula I provide very effective stabiliser packages in polyolefine formulations.

Some Examples will now be given. Parts and percentages are by weight unless otherwise stated.

EXAMPLE 1

A mixture of 15.70 part: of 2,2,6,6-tetramethylpiperidin-4-ol, 29.20 parts of methyl-β-(3,5-di-t-butyl-4-hydroxyphenyl) propionate and 1.00 part of lithium amide were stirred together in a melt at 150° C for five hours. The methanol formed during the reaction being removed using a modified Dean and Stark apparatus. The cooled reaction mass was subjected to column chromatography on an alumina column using petroleum ether as the solvent to yield the 2,2,6,6-tetramethylpiperidinyl-4-β-(3',5'-di-t-butyl-4'-hydroxy-phenyl) propionate as a white solid having a melting point of 77°–8° C and the following elemental analysis by weight:

|  | Found | Calculated for $C_{26}H_{43}NO_3$ |
|---|---|---|
| Carbon | 74.97 | 74.78 |
| Hydrogen | 10.37 | 10.38 |
| Nitrogen | 3.16 | 3.35 |

EXAMPLE 2

A mixture of 9.50 parts of 2,2,6,6-tetramethylpiperidin-4-ol and 9.50 parts of 3,5-di-t-butyl-4-hydroxybenzoyl chloride in 150 parts of dry benzene were heated under reflux conditions for six hours. The solution was allowed to cool and the white precipitate formed was removed by filtration. Removal of the benzene by distillation under reduced pressure yielded a yellow oil which slowly solidified; addition of ether precipitated a crystalline solid which was filtered, washed with ether and dried to give 2,2,6,6-tetramethylpiperidinyl-4-(3',5'-di-t-butyl-4'-hydroxy benzoate) as a white solid having a melting point of 180°–2° C and the following elemental analysis by weight:

|  | Found | Calculated for $C_{24}H_{39}NO_3$ |
|---|---|---|
| Carbon | 74.25 | 74.02 |
| Hydrogen | 9.84 | 10.03 |
| Nitrogen | 3.71 | 3.60 |

EXAMPLES 3 and 4

LIGHT STABILISATION TESTS 38 parts of polypropylene were homogenised with 0.076 part of n-octadecyl-β-(4'-hydroxy-3',5'-t-butylphenyl) propionate in a kneading machine over a period of 3 minutes at 200° C. 0.19 part of the product of Example 1 or 2, was then added and homogenisation continued for another 7 minutes.

This composition was compression moulded into films of 0.1 mm. thickness at 260° C for 6 minutes and the films so obtained were then quenched in cold water.

A section measuring 44× 100 mm. was separated from the 01 mm. annealed polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3000 Angstrom units; the blacklight lamps were 2 feet long, 20-watt ultraviolet lamps characterised by a peak emission of 3500 Angstrom units. The sample was rotated concentrically within the bank of lamps so that the radiation therefrom was uniformly distributed over the section under test.

The exposed sample was examined periodically and the time (T) at which the sample reached 50% of the initial elongation at break was noted.

For the purposes of comparison, similar tests were carried out on polypropylene samples consisting of, respectively:

(a) 38 parts of polypropylene and 0.076 part of n-octadecyl-β-(4'-hydroxy-3',5'-t-butylphenyl)propionate and (b) 38 parts of polypropylene, 0.076 part of n-octadecyl-β-(4'-hydroxy-3',5'-t-butylphenyl)propionate and 0.19 part of (2,2,6,6-tetramethylpiperidinyl-4)benzoate, which is a known light stabiliser described in German patent specification No. 1,929,928.

These comparative samples were prepared according to the foregoing procedure relating to the production of samples according to the invention.

The results obtained are set out in the following Table I.

HEAT STABILISATION TESTS 100 parts of unstabilised polypropylene powder were slurried with distilled acetone containing 0.5 parts of the product of Example 1 or 2. The acetone was then distilled off whilst agitating the slurry in a rotary evaporator.

The dried stabilised polypropylene powder was then passed at 200° C to a sheet of 1.25 mm. thickness.

The sheet was cut into strips (2.5 cm × 15 cm) and these strips were hung in an air-circulatory oven maintained at 150° C. The suspended strips were examined every hour for embrittlement which was determined by bending the end of a strip through 180° C, the bending being effected at a different point of the strip at each evaluation. The time at which the strip cracked (i.e. the failure time) was noted.

For the purposes of comparison, similar heat stabilisation tests were carried out on polypropylene samples consisting of respectively:

(a) 100 parts of polypropylene and
(b) 100 parts of polypropylene and 0.5 part of (2,2,6,6-tetramethylpiperidinyl-4)benzoate.

The results obtained are set out in the following Table I.

The results in Table I demonstrate that compounds of the present invention show marked superiority, as light and heat stabilisers for polypropylene, when compared with (2,2,6,6-tetramethylpiperidinyl-4)-benzoate - which is the closest related compound specifically described in the most pertinent prior art known viz. German Patent Application No. 1,929,928.

G.m.b.H.) using white cardboard as backing. In intervals of 200 hours of exposure time, 5 fibre samples were examined and their retained tensile strength determined. The data obtained were plotted graphically against exposure time and the exposure time (T) giving 50% loss of original tensile strength was derived from the graph. This value was taken as the failure time.

The data obtained are shown in the following Table II which also includes data relating to a control experiment (no light stabiliser) and data relating to a comparative experiment using a commercially-available light stabiliser.

TABLE II

| Example | Additive | Time (T) to 50% retained tensile strength (hours) | Factor $\frac{T \text{ (additive)}}{T \text{ (control)}}$ |
|---|---|---|---|
| — | none | 430 | 1 |
| — | 2-(2'-hydroxy-3',5'-di-t-butylphenyl)-5-chlorobenzotriazole | 530 | 1.2 |
| 5 | 2,2,6,6-tetramethyl-piperidinyl-4-β-(3',5'-di-t-butyl-4'-hydroxyphenyl)propionate | 1500 | 3.5 |

The improved light-stabilising effect produced by the compound of the invention compared with the effects produced in the control and comparative experiments is clearly seen from the data in Table II.

We claim:

1. A composition of matter stabilized against ultraviolet deterioration which comprises a synthetic organic polymer normally subject to ultraviolet deterioration containing from 0.1% to 2% by weight of the polymer of a stabilizing compound of the formula Table I

| Example | Additive | Time to embrittlement in heat-ageing test (hours) | Time to 50% of initial elongation at break in light-ageing test (hours) |
|---|---|---|---|
| — | None | 2 | 125 |
| — | 2,2,6,6-tetramethylpiperidinyl-4-benzoate | 2 | 330 |
| 3 | 2,2,6,6-tetramethylpiperidinyl-4-3',5'-di-t-butyl-4'-hydroxybenzoate | 11 | 437 |
| 4 | 2,2,6,6-tetramethylpiperidinyl-4-β-(3',5'-di-t-butyl-4'-hydroxyphenyl) propionate | 18 | 655 |

EXAMPLE 5

1000 Parts of unstablized polypropylene powder were thoroughly dry-blended with 1 part by weight of n-octadecyl-β-(4'-hydroxy-3',5'-di-t-butylphenyl) propionate and 2 parts by weight of the product of Example 1. The dry blend was extruded at cylinder temperatures of from 180° to 220° C and the resulting strand was granulated. The stabilised formulation so obtained was melt-spun and stretched under the following conditions:-

| Extruder temperatures | 230/265/275° C. |
|---|---|
| Melt temperature at the dye | 270° C. |
| Spinning speed | 400 m./minute |
| Stretching ratio | 1:5 |
| Titer of multifilament | 130/137 denier |
| Tensile strength | 6 g./denier |

The multifilament obtained was mounted on the sample holder of a Xenotest 150 apparatus (Quarzlampen

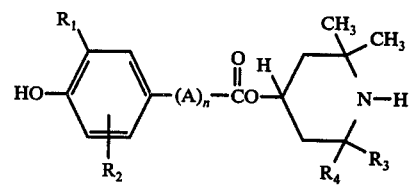

wherein A is $-CH_2-$, $-CH_2CH_2-$ or

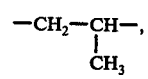

$R_1$ and $R_2$ are the same or different and each is a straight- or branched-chain alkyl group having from 1 to 6 carbon atoms, or 1-methylcyclohexyl or α,α-dimethylbenzyl, $R_3$ and $R_4$ ar the same or different and each is an alkyl group having from 1 to 12 carbon atoms or $R_3$ and $R_4$ together with the carbon atom to which they are bound form a saturated alicyclic residue having from 5 to 8 carbon atoms or the group of formula:

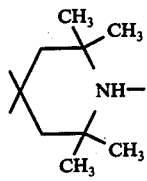

and n is 0 or 1.

2. A composition as claimed in claim 1, wherein the polymers is a polyolefine.

3. A composition of claim 2 wherein the polymer is polypropylene.

4. A composition according to claim 2 wherein the stabilizer is of the formula

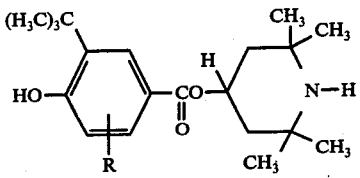

wherein R is a straight- or branched-chain alkyl group having from 1 to 6 carbon atoms.

5. A composition according to claim 2 wherein the stabilizer is of the formula

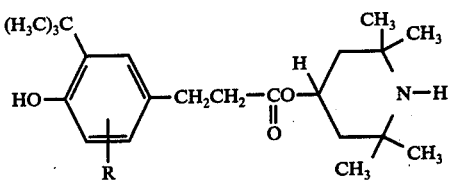

wherein R is a straight- or branched-chain alkyl group having from 1 to 6 carbon atoms.

6. A composition of claim 2 wherein the stabilizer is 2,2,6,6-tetramethylpiperidinyl-4-3',5'-di-t-butyl-4'-hydroxybenzoate.

7. A composition of claim 2 wherein the stabilizer is 2,2,6,6-tetramethylpiperidinyl-4-β-(3',5'-di-t-butyl-4'-hydroxyphenyl)-propionate.

* * * * *